United States Patent [19]
Ruiz

[11] Patent Number: 5,766,944
[45] Date of Patent: Jun. 16, 1998

[54] T CELL DIFFERENTIATION OF CD34+ STEM CELLS IN CULTURED THYMIC EPITHELIAL FRAGMENTS

[76] Inventor: Margaret Eileen Ruiz, 4202 E. West Highway, Chevy Chase, Md. 20815

[21] Appl. No.: 775,509

[22] Filed: Dec. 31, 1996

[51] Int. Cl.$^6$ .................................................. C12N 5/08
[52] U.S. Cl. .................. 435/325; 435/339.1; 435/347; 435/355; 435/372; 435/372.3; 435/373; 435/384; 435/386
[58] Field of Search .............................. 435/325, 339.1, 435/347, 355, 372, 372.3, 373, 382, 384, 386

[56] References Cited

PUBLICATIONS

Margaret Ruiz, Stanford Roodman, John Bouhasin, Alan Knutson, *T Cell Differentiation/Maturation of CD34+ Stem Cell from HIV–Seropositive Hemophiliacs in Cultured Thymic Epithelial Fragments*, Stem Cells 14, 132–145 (1996).

M. Rosenzweig, D.F. Marks, H. Zhu, D. Hempel, K.G. Mansfield, P.K. Sehgal, S. Kalams, D.T. Scadden, and R.P. Johnson, *In Vitro T Lymphopoiesis of Human and Rhesus CD34+ Progenitor Cells*, Blood 87, No. 10, 4040–4048 (1996).

Geir Erland Tjonnfjord, O.P. Veiby, R. Steen, & T. Egeland, *T Lymphocyte Differentiation In Vitro from Adult Human Prethymic CD34+ Bone Marrow Cells*, J. Exp. Med. 177, 1531–1539 (1993).

Andrew R. Freedman, H. Zhu, J.D. Levine, S. Kalams, & D.T. Scadden, *Generation of human T lymphocytes from bone marrow CD34+ cells in vitro*, Nature Medicine 2, No. 1, 46–51 (1996).

Michael Rosenzweig, E.M. Bunting, R.L. Damico, D.P. Clark, & G.N. Gaulton, *Human Neonatal Thymic Organ Culture: An ex vivo Model of Thymocyte Ontogeny and HIV–1 Infection*, Pathobiology 62, 245–251 (1994).

John M. Dwyer, C. C. Wood, J. McNamara, B. Kindler, *Transplantation of Thymic Tissue into Patients with AIDS*, Arc Intern Med. vol. 147, 513–517 (1987).

Margaret E. Ruiz, J. Freeman, J.D. Bouhasin, A.P. Knutsen, M.J.C. Hendrix, *Arrest of In Vitro T Cell Differentiation of Normal Bone Marrow–Derived CD34+ Stem Cells with Thymic Epithelial Fragments from Children with AIDS*, Stem Cells 14, 533–547 (1996).

Alan P. Knutsen, S.T. Roodman, M.E. Ruiz, K.R. Mueller, J.D. Bouhasin, *Development of a Method of Thymocyte Differentiation of Bone Marrow–Enriched CD34+CD38– Cells in Postnatal Allogeneic Cultured Thymic Epithelia to Evaluate Immunodeficiency Disorders*, Stem Cells 14, 702–713 (1996).

Bruno Peault, I.L. Weissman, C. Baum, J.M. McCune, A. Tsukamoto, *Lymphoid Reconstitution of the Human Fetal thymus in SCID Mice with CD++ Precursor Cells*, J. Exp. Med. The Rockefeller University Press vol. 174, 1283–1286 (1991).

Jean–marie Dupuy, N. Gilmore, H. Goldman, C. Tsoukas, D. Pekovic, J.P. Chausseau, R. Duperval, M. Joly, L. Pelletier, Y. Thibaudeau, *Thymic Epithelial Cell Transplantation in Patients with Acquired Immunodeficiency Syndrome*, Thymus 17, 205–218 (1991).

Sven A. Danner, B.J. Schuurman, J.M.A. Lange, F.H.J. Gmelig Meyling, P.Th.A. Schellekes, J. Huber, L. Kater, *Implantation of cultured Thymic Fragments in Patients with Acquired Immunodeficiency Syndrome*, Arch Intern Med vol. 146, 1133–1138, (1986).

Primary Examiner—Laurie Scheiner
Attorney, Agent, or Firm—The Firm of Gordon W. Hueschen

[57] ABSTRACT

A procedure for carrying out T cell differentiation of CD34+ stem cells in an in vitro culture of thymic epithelial fragments whereby the differentiated T cells achieve full immunocompetence. The invention also includes the procedure for differentiation of stem cells from HIV seropositive individuals or genetically modified stem cells. The invention broadly relates to the culture of cultured thymic epithelial fragments and provides procedures for verifying true immunocompetence of the resulting T cells and for analyzing the effects of various compounds on the differentiation process. The invention also comprises several novel applications for utilizing the procedure of the invention, including grafting fortified cultured thymic epithelial fragments and infusing immunocompetent T cells into patients with compromised immune systems.

4 Claims, No Drawings

T CELL DIFFERENTIATION OF CD34+ STEM CELLS IN CULTURED THYMIC EPITHELIAL FRAGMENTS

BACKGROUND OF THE INVENTION

Field of Invention

Acquired ImmunoDeficiency Syndrome (AIDS) is manifested by recurrent microbial infections and malignancies as the result of a progressive cellular and humoral dysfunction caused by Human ImmunoDeficiency Virus (HIV) infection. AIDS results in a generally diminished capacity to maintain immunity to infection, caused in part by T cell immune deficiency. In particular, T cell immune deficiency is characterized by the dysfunction and eventual depletion of $CD4^+$ T helper cells.

The generation of CD4+ T cells has been shown to originate primarily from the peripheral lymphoid pool during HIV infection with none derived from the central thymic compartment. (D. D. Ho, A. U. Neumann, A. S. Perelson, W. Chen, J. M. Leonard, and M. Markowitz, Rapid turnover of Plasma virions and CD4 lymphocytes in HIV-1 infection, Nature 373, 123-126 (1995); X. Wei, S. K. Ghosh, M. E. Taylor, V. A. Johnson, E. A. Emini, P. Deutsch, J. D. Lifson, S. Bonhoeffer, M. A. Nowak, B. H. Hahn, M. S. Saag, and G. M. Shaw, Viral dynamics in human ImmunoDeficiency virus type 1 infection, Nature 373, 117-122 (1995)) Mature resident CD4+ lymphocytes can be expanded in the peripheral T cell pool, but this population has a limited proliferation potential. (H. Vaziri, W. Dragowska, R. C. Allsop et al., Evidence for a mitotic clock in human hematooocetic stem cells; Loss of telomeric DNA with age, Proc Natl Acad Sci 91, 9857-9860 (1994))

The thymus is dependent on a continual supply of bone marrow derived stem cells to maintain both lymphopoiesis and the integrity of the thymic stromal microenvironment. HIV disrupts the peripheral lymph node architecture with cellular depletion and collapse of the follicular dendritic cell network. In addition, HIV infection disrupts the bone marrow and the thymic microenvironments which become incapable of regenerating the lymphoid populations destroyed by the HIV virus.

Bone marrow hematopoietic progenitor cells of lymphocytes, erythrocytes and myeloid cells are affected by HIV infection, contributing to a decrease in lymphopoiesis. The CD34+ stem cell population of the bone marrow is a heterogeneous mixture of progenitors, in which only a minor percentage represents the prelymphoid subset. There is an even smaller percentage (0.01%) of CD34+ stem cells constituting the totipotent stem cell population that is responsible for maintaining the hematopoietic steady state. The in vitro growth of CD34+ stem cells is inhibited by HIV or its products, and this HIV-induced suppression of progenitor cells may adversely affect the bone marrow capacity to support lymphopoiesis. (H. N. Steinberg, C. S. Crumpacker, P. A. Chatis, In vitro Suppression of normal human bone marrow progenitor cells by human Immuno-Deficiency virus, J. Virol 65, 1765-1769 (1991); K. Mehta, P. Gascon, S. Roboy, The gelatinous bone marrow (serous atrophy) in patients with Acquired ImmunoDeficiency Syndrome, evidence of excess sulfated glycosaminoglycan, Arch Pathol Lab Med 116, 504-508 (1992); G. Zauli, M. C. Re, G. Visani, et al., Inhibitory effect of HIV-1 envelope glycoproteins gp 120 and gp 160 on the in vitro growth of enriched (CD34+) hematopoietic progenitor cells, Arch Virol 122, 271-280 (1992); G. Zauli, M. C. Re, B. Davis, et al., Impaired in vitro growth of purified (CD34+) hematopoietic progenitors in human ImmunoDeficiency virus-1 seropositive thrombocytopenic individuals. Blood 79, 2680-2687 (1992))

The thymus is essential for differentiation of progenitor thymocytes into mature T cells. HIV infection is manifested in the thymus by loss of thymocytes, loss of corticomedullary differentiation and calcification of Hassall's corpuscles. In addition to this direct depletion, regeneration de novo of lymphocytes by thymopoiesis is compromised.

The thymus microenvironment is adversely affected by HIV. Infection of resident T cells, thymocytes, CD34+ CD4+ stem cells and thymic epithelial cells specifically affect the generation of naive CD4+ T cells by thymopoiesis. The thymus manifests a loss of thymocytes due to direct infection. (G. Zauli, M. C. Re, B. Davis, et al., Impaired in vitro growth of purified (CD34+) hematopoietic progenitors in human ImmunoDeficiency virus-1 seropositive thrombocytopenic individuals. Blood 79, 2680-2687 (1992); M. L. Bonyhadi, L. Rabin, S. Salimi, et al., HIV induces thymus depletion in vivo. Nature 363, 728-732 (1993); G. M. Aldrovandi, G. Feuer, L. Gao, et al., The SCID-hu mouse as a model for HIV-1 infection, Nature 363, 732-735 (1993); E. F. Hays, C. H. Uittenbogaart, J. C. Brewer, et al., In vitro studies of HIV-1 expression in thymocytes from infants and children, AIDS 6, 265-269 (1992)) Thymic epithelial cells can be infected with HIV resulting in their dysfunction and destruction. (S. M. Schnittman, K. H. Singer, J. J. Greenhouse, et al., Thymic microenvironment induces HIV infection. Physiologic secretion of Il-6 by thymic epithelial cells up-regulates virus expression in chronically infected cells, J Immunol 147, 2553-2558 (1991); K. Numazake, H. Goldman, X-Q Bai, et al., HIV-1, cytomegalovirus, and human ImmunoDeficiency virus on cultured human thymic epithelial cells, Microbiol Immunol 33, 773-745 (1989)) The thymic stromal architecture becomes dysplastic, displaying an effacement of the cortical thymic epithelium, a loss of corticomedullary differentiation, a loss of Hassall's corpuscles, thymic epithelial necrosis or calcification, and hyaline changes of the pervascular spaces. (T. A. Seemayer, A. C. Laroche, H. Y. Goldman, Precocious thymic involution manifest by epithelial injury in acquired immune deficiency syndrome. Hum Path 15, 469-474 (1984); T. A. Seemayer, W. Lapointe, J. Michaud, et al., The thymus in the acquired ImmunoDeficiency syndrome: Pathological and theoretical consideration, In: Griselli and Vossen, eds. Progress in ImmunoDeficiency Research and Therapy, Elsevier Publisher, 171-190 (1984); W. M. Savino, M. Dardenne, C. Marche, et al., Thymic epithelium in AIDS: An immunohistologic study, Am J Path 122, 302-7 (1985); H. J. Schuurman, W. J. A. Krone, R. Broekhuizen, et al., The thymus in AIDS, Am J Path 134, 1329-1338 (1980); H. J. Schuurman, J. van Baarlen, W. J. A. Krone, et al., The thymus in the acquired immuno-deficiency syndrome, In: Kendall M. and Ritter M. eds. The microenvironment of the human thymus. Chapter 9. Harwood Academic Publishers (1988); V. V. Joshi, J. M. Oleske, Pathologic appraisal of the thymus gland in acquired ImmunoDeficiency syndrome in children, a study of four cases and a review of the literature, Arch Pathol Lab Med 109, 142-146 (1985); C. Nezelof, Invited Review: Thymic pathology in primary and secondary immunodeficiencies, Histopath 21, 499-511 (1992)) Morphologically, the epithelium may be represented as sheets of undifferentiated cells called guirlandes. (W. M. Savino, M. Dardenne, C. Marche, et al., Thymic epithelium in AIDS: An immunohistologic study, Am J Path 122, 302-7 (1985); H. J. Schuurman, J. van Baarlen, W. J. A. Krone, et al., The thymus in the acquired immunodeficiency syndrome. In: Kendall M. and Ritter M. eds. The microenvironment of the human thymus. Chapter 9. Harwood Academic Publishers. (1988))

Prior Art

In adult patients, HIV production and clearance occur continuously throughout HIV-infection driving a continuous turnover of CD4+ T cells primarily from the peripheral lymphoid pool. This loss is progressive without any discernable contribution from the thymic compartment. Therefore, immune enhancement or reconstitution of the T cell compartment is being studied for the treatment of patients with AIDS to prevent susceptibility to infections and malignancies. This process involves thymic transplantation or augmentation of residual thymic function.

Previously, researchers have transplanted cultured thymic epithelial fragment tissue into patients with AIDS to replace thymic function. (S. A. Danner, H. J. Schuurman, J. M. A. Lange, et. al., Implantation of cultured thymic epithelial fragments in Patients with acquired ImmunoDeficiency syndrome, Arch Intern Med. 146, 1133–1136 (1986); J. M. Dwyer, C. C. Wood, J. McNamara, et al., Transplantation of thymic tissue into patients with AIDS, Arch Intern Med 147, 513–517 (1987); J. M. Dupuy, N. Gilmore, H. Goldman, et al., Thymic epithelial cell transplantation in Patients with acquired ImmunoDeficiency syndrome, Thymus 17, 205–218 (1991)) No sustainable increase of T cell numbers was observed. The reasons for graft failure were not clear, although theoretically could have been due to rejection, inadequate numbers of pre-T stem cells capable of homing or entering the thymus, HIV infection of newly differentiating thymocytes, or HIV infection of thymic epithelial cells or dendritic cells resulting in their dysfunction or destruction.

Thymic biopsy studies obtained by two groups revealed the absence of thymic epithelial tissue with HIV infected T cells at the graft site or with thymic epithelial tissue present but involved in a multinucleated giant cell inflammatory response. (S. A. Danner, H. J. Schuurman, J. M. A. Lange, et al., Implantation of cultured thymic epithelial fragments in patients with acquired ImmunoDeficiency syndrome, Arch Intern Med 146, 1133–1136 (1986); J. M. Dwyer, C. C. Wood, J. McNamara, et al., Transplantation of thymic tissue into patients with AIDS, Arch Intern Med 147, 513–517 (1987)) These biopsy results suggest that the thymic epithelial tissue was being damaged by an ongoing T cell mediated inflammatory response due to HIV infection rather than being involved in rejection.

Supporting this contention are in vitro studies which demonstrate that HIV infected thymocytes and T cells induce thymic epithelial failure in lentiviral infection. (R. Hong, Thymus transplantation in HIV-1 infected children and SIV infected rhesus, Novel HIV therapies; From Discovery to Clinical Proof of Concept. Spirat Conference Bethesda, Md. July 1995) In a study of the efficacy of thymus transplantation in an SIV-infected rhesus, one animal which had previously received a T cell depleted human cultured thymic epithelial cell fragment transplant succumbed to an Mycobacterium avium intracellular infection. At autopsy, the monkey thymus demonstrated many hyalinized lobules, appeared atrophic and devoid of lymphocytes, but did not appear morphologically stressed. The transplanted human cultured thymic epithelial cell fragment was replenished with monkey lymphocytes, thus illustrating the SIV infected host bone marrow microenvironment was capable of repopulating a transplanted (human donor) thymus. Similarly, the host thymus capacity for attracting or retaining stem cells could have been functionally altered by the lentiviral infection.

Research in the augmentation of thymic function extends to the possibility of culturing thymic tissue in vitro, exposing naive T cell progenitor cells to the thymus for differentiation and maturation, and then explanting the immunocompetent T cells into the HIV-affected individual.

Mouse T cell ontogenists have developed in vivo fetal thymic culture systems whereby T cell progenitor cells are microinjected into human thymic grafts transplanted into mice with "Severe Combined ImmunoDeficiency" (SCID-hu mice). (B. Peault, I. L. Weissman, C. Baum, J. M. McCune, & A. Tsukamoto, Lymphoid reconstitution of the human fetal thymus in SCID mice with CD34+ precursor cells, J. Ext. Med. 174, 1283–1286 (1991))

These murine systems have been useful for monitoring drug effects for human HIV therapy, but lack in the ability to monitor effects of various HIV therapeutics on discrete T cell differentiation stages. Further Xenogeneic (inter species) systems have been developed which more closely resemble the human thymic microenvironment. Unlike the murine models, T cells derived from Rhesus cultured thymic stromal cells acquire cell surface markers characteristic of normal T-lymphopoiesis. (M. Rosenzweig, D. F. Marks, H. Zhu, D. Hempel, K. G. Mansfield, P. K. Sehgal, S. Kalams, D. T. Scadden, and R. P. Johnson, In Vitro T Lymphopoiesis of Human and Rhesus CD34+ Progenitor Cells, Blood 87, No. 10, 4040–4048 (1996)) However, clinical application will be hampered due to FDA resistance to permit Xeno-transplantation such as the use of Rhesus thymic implantation.

The study of T cell differentiation in man has been hampered by the difficulty of maintaining human thymus in culture. Most human culture systems to date have all employed thymic epithelial monolayers, that is a single cell layer composed of cells which are derived from explanted tissue. These studies have shown that adherent thymic stromal cell monolayers are capable of maturing lympho-hemopoietic stem cells into T-lymphocytes expressing surface T cell marker CD4+. (Geir Erland Tjonnfjord, O. P. Veiby, R. Steen, & T. Egeland, T Lymphocyte Differentiation In Vitro from Adult Human Prethymic CD34+ Bone Marrow Cells, J. Exp. Med. 177, 1531–1539 (1993), see also Andrew R. Freedman, H. Zhu, J. D. Levine, S. Kalams, & D. T. Scadden, Generation of human T lymphocytes from bone marrow CD34+ cells in vitro, Nature Medicine 2, No. 1, 46–51 (1996))

The T cells generated from monolayer cultures are deprived of the sequential migratory signals which they would normally encounter in the natural thymus microenvironment. There are discrete differentiation stages which are accomplished by the selected migration from the cortical regions to the medullary regions of the thymus, a sort of graduated educational experience in which the developing T cell becomes immunocompetent. T cells which mature on a monolayer may resemble phenotypically mature cells, i.e. expressing markers identifying them as T cells, however to date no work has demonstrated T cells derived from thymic monolayers are immunocompetent.

Thus far, the only non-monolayer culture system involved a crude preparation of thymus pieces cultivated for a short-term (up to 14 days). This culture of thymus fragments exhibited evidence of mature T cells resident in the cultured fragments which progressively declined over the culture period. (Michael Rosenzweig, E. M. Bunting, R. L. Damico, D. P. Clark, & G. N. Gaulton, Human Neonatal Thymic Organ Culture: An ex vivo Model of Thymocyte Ontogeny and HIV-1 Infection. Pathobiology 62, 245–251 (1994)) These studies were limited in that the thymus fragments only possessed the progenitor thymocytes already present at the thymus when cultured. No infused progenitor cells were actually brought to maturity.

OBJECTS OF THE INVENTION

With this invention, it has been discovered that under appropriate conditions, which are a novel and unobvious aspect of this invention, allogeneic thymic epithelial fragments are cultured in vitro providing a microenvironment, expressing discrete phenotypical regions, i.e. subpopulations of thymic epithelial and mesenchymal tissue.

It has been discovered that under appropriate conditions, which are a novel and unobvious aspect of this invention, enriched bone marrow derived CD34+ Stem cells obtained by aspiration from individuals not infected with HIV may be cocultured in vitro in this thymic microenvironment formed by cultured thymic epithelial fragments to the point of differentiation into functional T cells capable of the immunocompetence associated with T cells typically produced in vivo.

It is also an object of the present invention to provide a novel and unobvious process whereby enriched bone marrow derived CD34+ Stem cells obtained by aspiration from individuals infected with HIV may be cocultured in vitro in this thymic microenvironment formed by cultured thymic epithelial fragments to the point of differentiation into functional T cells capable of the immunocompetence associated with T cells typically produced in vivo.

The present invention also pertains to a novel and unobvious process whereby enriched CD34+ Stem cells obtained by aspiration from normal volunteers may be cocultured with thymic epithelial fragments cultured from individuals infected with HIV to the point of differentiation into functional T cells to enable evaluation of HIV-induced thymic pathogenesis.

It is a further object to provide a method of sequential phenotypic analysis of stem cell/cultured thymic epithelial fragment coculture progeny to enable the evaluation of the effects of putative HIV therapy.

It is an additional object to provide a method of treating individuals infected with HIV whereby CD34+ stem cells isolated from the purified bone marrow of HIV-seropositive individuals are co-cultured with a non-infected thymic microenvironment to induce differentiation of CD34+ stem cells into functional T cells for potential re-infusion into the HIV-affected individual or alternatively to provide a T cell reconstituted thymic microenvironment for immune engraftment (thymic transplantation).

SUMMARY OF THE INVENTION

What is believed to be the invention, then, inter alia, comprises the following, singly or in combination:
A process of coculturing Cultured Thymic Epithelial Fragments and bone-marrow derived stem cells whereby the stem cells are differentiated into immunocompetent T cells, comprising the following steps:

establishing cultured thymic epithelial fragment cultures by:

excising thymus tissue as a metabolic specimen avoiding mechanical pressure and heat cauterization and placing the tissue in chilled media, removing the thymic capsule from the excised thymic tissue, mincing the tissue into small fragments and agitating the fragments in complete media to wash out thymocytes, depleting thymocytes and hematopoietic cells including dendritic cells by incubating the fragments on sterile tissue rafts which are partially immersed in complete medium supplemented with 2'-deoxyguanosine (preferably about 1.35 mM), at 37 C. in a partial $CO_2$ atmosphere (preferably about 5%), and culturing the T cell depleted fragments to optimize stromal viability in complete medium supplemented with hydrocortisone (preferably about 0.4 μg/ml), epidermal growth factor (preferably about 11 ng/ml), cholera enterotoxin (preferably about $1\times10^{-10}$M), insulin (preferably about 5 μg/ml), adenine (preferably about $1.8\times10^{-4}$ g/ml), and sodium pyruvate (preferably about $1.8\times10^{-4}$ g/ml), isolating CD34+CD38– stem cells by:

performing Ficoll-Hypaque density centrifugation to obtain nucleated bone marrow cells from bone marrow aspirates diluted in normal saline, depleting CD2+ lymphocytes by rosette formation with sheep Red Blood Cells treated with 2-amino-ethyl isothiouronium bromide, followed by a second Ficoll-Hypaque density centrifugation, removing non-CD34 cells by culture with monoclonal antibodies or immunomagnetic microbeads, followed by separation over a monoclonal antibody-coated panning flask or magnetic column, and coculturing the Cultured Thymic Epithelial Fragments and purified CD34+CD38– Stem Cells by:

seeding CD34+CD38– stem cells by infusion onto the surface of the Cultured Thymic Epithelial Fragments in transwell plates in Iscove's/Ham's medium (preferably at a 1:1 ratio) containing IL-2 (preferably about 25 U/ml) at about 37° C. in a partial $CO_2$ atmosphere (preferably about 5%) until differentiated into mature T cells, replacing medium every few days (preferably about 4), and isolating the differentiated T cells by aspirating the cells from the culture wells, washing, resuspending in saline, subjecting the cells to Ficoll-Hypaque density centrifugation to remove dead cells, washing the mononuclear cells, and resuspending the pure mononuclear cells in saline.

Also, a process of coculturing Allogeneic Cultured Thymic Epithelial Fragments and bone-marrow derived stem cells from HIV seropositive patients whereby the stem cells are differentiated into immunocompetent T cells free of HIV infection, comprising the following steps:

establishing cultured thymic epithelial fragment cultures by:

excising thymus tissue as a metabolic specimen avoiding mechanical pressure and heat cauterization and placing the tissue in chilled media, removing the thymic capsule from the excised thymic tissue, mincing the tissue into small fragments and agitating the fragments in complete media to wash out thymocytes, depleting thymocytes and hematopoietic cells including dendritic cells by incubating the fragments on sterile tissue rafts which are partially immersed in complete medium supplemented with 2'-deoxyguanosine (preferably about 1.35 mM), at 37 C. in a partial $CO_2$ atmosphere (preferably about 5%) for several days (preferably about seven days), and culturing the T cell depleted fragments to optimize stromal viability in complete medium supplemented with hydrocortisone (preferably about 0.4 µg/ml), epidermal growth factor (preferably about 11 ng/ml), cholera enterotoxin (preferably about $1\times10^{-10}$M), insulin (preferably about 5 µg/ml), adenine (preferably about $1.8\times10^{-4}$ g/ml), and sodium pyruvate (preferably about $1.8\times10^{-4}$ g/ml), isolating CD34+ stem cells from HIV seropositive patients by:
  collecting bone marrow from aspirates in Heparinized tubes,
  performing Ficoll-Hypaque density centrifugation to obtain nucleated bone marrow cells from bone marrow aspirates diluted in normal saline,
  depleting CD2+ lymphocytes by rosette formation with sheep Red Blood Cells treated with 2-amino-ethyl isothiouronium bromide, followed by a second Ficoll-Hypaque density centrifugation,
  removing macrophage/monocytic cells by adherence on plastic Petri dishes,
  removing non-CD34 cells by culture with monoclonal antibodies or immunomagnetic microbeads, followed by separation over a monoclonal antibody coated panning flask or magnetic column, and coculturing the Cultured Thymic Epithelial Fragments and purified CD34+CD38– Stem Cells by:
  seeding a minimum of 5,000 lineage negative stem cells or 50,000 lineage committed stem cells by infusion onto the surface of the Cultured Thymic Epithelial Fragments in transwell plates in Iscove's/Ham's medium (preferably at a 1:1 ratio) containing IL-2 (preferably about 25 U/ml) at about 37° C. in a partial $CO_2$ atmosphere (preferably about 5%) until differentiated into mature T cells, replacing medium every few days (preferably about 4), and
  isolating the differentiated T cells by aspirating the cells from the culture wells, washing, resuspending in saline, subjecting the cells to Ficoll-Hypaque density centrifugation to remove dead cells, washing the mononuclear cells, and
  resuspending the pure mononuclear cells in saline.

Also, a process whereby thymic microenvironmental performance (i.e. thymopoiesis) may be evaluated comprising the step of carrying out the process of claim 1 or claim 2 in the presence of a compound proposed to be used for HIV therapy to determine if the stem cell differentiation is inhibited or otherwise altered in the presence of said compound.

Also, a method-of-treating a human patient infected with HIV using autologous (patient) bone marrow-derived stem cells which have been expanded in coculture with Cultured Thymic Epithelial Fragments into immunocompetent T cells comprising the step of transplanting the reconstituted thymus tissue as a graft into said patient to restore immune function and reduce the immunosuppression caused by AIDS.

Also, a method-of-treating a human patient infected with HIV using autologous (patient) bone marrow-derived stem cells which have been expanded in coculture with Cultured Thymic Epithelial Fragments into immunocompetent T cells comprising the step of administering said T cells via intravenous infusion into said patient to restore immune function and reduce the immunosuppression caused by AIDS.

Also, a process of expanding and differentiating bone marrow-derived stem cells into immunocompetent T cells comprising the step of coculturing the stem cells in an in vitro Cultured Thymic Epithelial Fragment 3-D microenvironment which comprises more than a Thymic Epithelial Cell Monolayer.

Also, a process whereby thymic microenvironmental performance (i.e. thymopoiesis) may be evaluated comprising the step of carrying out the process of claim 1 in the presence of genetically modified stem cells containing HIV protective genes to determine if the stem cell differentiation is inhibited, immunocompetence is achieved, and whether the resulting T cells are resistant to HIV infection.

DESCRIPTION OF THE PREFERRED EMBODIMENTS

CULTURE OF THYMIC EPITHELIAL FRAGMENTS

The present invention provides a method for the Culture of Thymic Epithelial fragments into a microenvironment expressing discrete phenotypical regions, i.e. subpopulations of thymic epithelial and mesenchymal tissue. Thymic Epithelial Fragment cultures are established by explant and subculture. In order to maximize thymic epithelial cell recovery for long term cell culture, the thymic tissue is treated as a metabolic specimen, requiring prompt removal and expedient transport. The thymus gland should be removed without harming the tissue by undue manual/mechanical pressure or heat with cauterization. The specimen is then placed in a generous volume of chilled fully supplemented complete media (such as Dulbecco's modified Eagle's medium (DMEM) (GIBCO, BRL, Grand Island, N.Y.), RPMI-10, or HAM's F12+ supplements) supplemented with 5% heat inactivated fetal calf serum (FCS). The external capsule is thoroughly removed using blunt dissection technique with the forceps and scissors, any hemorrhagic/necrotic areas and any notable vessels and the interlobular connective tissue are removed.

The thymus tissue is then divided with a sterile scalpel into lobules by identifying the natural anatomical fascial planes present between the lobules. These sections are further sliced into long thin pieces and agitated gently in the media to wash out as many thymocytes as possible.

Thymocytes and other hematopoietic cells, including dendritic cells, are then depleted by incubation in a 1.35 mM 2'-deoxyguanosine supplemented media (Ham's F-12 medium supplemented with 10% FCS, 1.35 mM 2'-deoxyguanosine, 25 mM HEPES, 2 mM glutamine, 50 U/ml penicillin, and 1 µg/ml streptomycin (complete medium)). The Cultured Thymic Epithelial Fragments are incubated on sterile gelfoam tissue rafts (1 cm×3 cm) set in 6 cm petri dishes. Tissue rafts are prepared by partially immersing the gelfoam in the deoxyguanosine media. The fluid level in the Tissue Culture plate should be adjusted so that the deoxyguanosine media is about ⅔ the height of the gelfoam (the tissue should not be in direct contact with the deoxyguanosine media as it is toxic to both thymocytes and stroma). The thymus fragments are arranged on the gelfoam/filter tissue raft allowing a small rim of free space between adjoining fragments. The tissue fragments are then incubated in a fully humidified incubator (5% $CO_2$ atmosphere) at 37° C. for two weeks.

The deoxyguanosine media should be changed every day for the first three days and every third day until the thymocyte depletion is completed. Depletion of the thymus slices generally takes about 1 to 2 weeks, but may need to be adjusted depending on the thickness of the slices. To assess the degree of depletion during the culture period, a portion of several of the thymus slices can be harvested and processed for histology, cytokeratin staining and T cell markers by immunofluorescence.

During the first few days of thymocyte depletion, thymocytes emigrate in massive numbers and the slices may need to be rinsed with sterile saline or media to maintain an optimal tissue surface for gas/nutrient exchange. At the completion of the thymocyte depletion phase, the thymus tubular slices should be cut into smaller pieces. The thymic epithelial fragments (TEF) for culture should be approximately 2 mm×1 mm in size. The fragments are then cultured in the TEF media approximately 7 days, checking periodically under the microscope to see if the edges of any fragments are forming epithelial skirts. (TEF media comprises: 67% DMEM, 22% HAM's F-12, 5% heat inactivated FCS, $1.07\times10^{-6}$M Hydrocortisone, $10^{-10}$M Cholera Toxin, $7\times10^{-7}$M Insulin, $1.8\times10^{-4}$M Adenine, 1 mM Sodium Pyruvate, 11.2 ng/ml EGF). Occasionally, certain thymus tissue will begin to show signs of early tissue damage, which can be identified as cystic degeneration microscopically. The fragments which begin to show signs of cystic degeneration during the TEF culture period should not be used for long term coculture with purified stem cells. Suboptimal tissue should be removed and discarded.

ISOLATION OF CD34+ STEM CELLS

The CD34+ molecule is a single chain type I transmembrane glycoprotein serving as a differentiation stage specific receptor which is associated with hematopoietic progenitor cells, stromal cell precursors, and microvascular endothelial cells. The CD34+ stem cell population is composed of a heterogeneous mixture of cell types, the major fraction represent committed progenitors and a minor fraction of CD34+ stem cells which are capable of generating hematopoietic progenitor cells in long term culture. Bone marrow is the richest source of CD34+ cells (1–3% in normal individuals).

Bone marrow aspirates are obtained and diluted 1:2 with sterile PBS or normal saline and mixed gently. Depletion of Red Blood Cell/high density cells is accomplished by the addition of an equal volume of 3% gelatin which is mixed gently and allowed to settle by gravity sedimentation. Sedimentation time may vary with different donors and the quality of the marrow aspirate. When the Red Blood Cell fraction occupies 20% of the initial volume and there is a definite interface between the leukocyte rich plasma layer and the Sedimented Red Blood Cell (SRBC) layer, the nuclear cells can be harvested by pipetting the plasma layer into 50 ml tubes. Cells are washed with NS or PBS and centrifuged at 1350 rpm.

The RBC depleted fraction is resuspended in 35 ml complete media (such as Dulbecco's modified Eagle's medium (DMEM) (GIBCO, BRL, Grand Island, N.Y.), RPMI-10, or HAM's F12+ supplements)(to approximate the 1 to 3.5 dilution of whole blood for Ficoll Hypaque), which is then underlaid with 15 ml of Ficoll Hypaque (d=1.077 g/ml) for low density cell centrifugation. The Ficoll Hypaque gradient is then centrifuged at 1350 rpm (400 G) at room temperature (22° C.) for 35 minutes. Then, the interface mononuclear cells are harvested with a pipette. The mononuclear cells are then diluted with an equal volume of PBS, spun at 1000 rpm for 10 minutes, and the supernatant is aspirated and discarded. The cells are resuspended in PBS +2% FCS, spun and aspirated two more times. The mononuclear marrow cells are resuspended in 5 ml RPMI and counted. The mononuclear marrow cell concentration is then adjusted to $10\times10^6$ cells/ ml with RPMI-5%HI-ADS-FCS (note-maximum of $70\times10^6$ cells/tube).

A 0.14M 2-Aminoethylisothiouronium bromide (AET) solution is prepared and mixed 4:1 with Sedimented Red Blood Cells (SRBC) and incubated at 37° C. for twenty minutes. The AET treated SRBC's (AET-SRBC) are then washed four times with PBS. A 1% AET-SRBC solution is prepared by diluting 0.5 ml of packed AET-SRBC with 50 ml PBS. An equal volume of the 1% AET-SRBC solution is then added to the mononuclear marrow cell suspension and the mixture is incubated at 37° C. for 5 minutes. Centrifuge the cell mixture at 600 rpm for 5 minutes then incubate at 4° C. for 60 minutes. [Alternately, a 2% AET-SRBC solution mixed with a cell suspension of $2.5\times10^6$ cells/ml can be used to deplete CD2+ T cells, a sample of the rosetting cells can be checked under the microscope as rapid rosetting with large agglutination may entrap non-T cells (the percent rosetting should not exceed that of a $t_o$ sample). ]

After the one hour incubation, the cells are gently resuspended so as not to shear the CD2/CD58 complex between T cells/SRBC. The cell suspension is gently underlaid with a volume of Ficoll-Hypaque which is 2× the cell suspension volume. The F/H gradient is centrifuged at 600 rpm for 10 minutes and then at 1350 rpm for 25 minutes. The T cells are located in the pellet and the non-T cells (B cells, macrophages/dendritic cells, mixed stem cell population including CD34+ cells) are located at the interface. Harvest the interface mononuclear cells with a pipette. Dilute the cells with an equal volume of PBS, centrifuge at 1000 rpm for 10 minutes, aspirate and discard the supernatant. Repeat wash again.

The cells are then resuspended in complete RPMI (without serum) and the cell concentration is adjusted to $2\times10^6$ cells/ml. Non-CD34 cells are then depleted by immunomagnetic selection.

Resuspend the cells in 2–3 ml complete media and perform a cell count. Calculate CD34+ cell recovery. Reserve an aliquot for Colony Forming Unit Assays/ phenotyping in a separate tube with complete media. The CD34+ cells may have sheared epitopes and/or down regulation of the receptor induced by the binding of the capture Ab. The CD34+ receptor should recycle within 24–36 hours after binding to the capture Ab in the selection process. The aliquot reserved for phenotyping should therefore be rested prior to testing. There may be considerable variability in detection of the CD34 receptor among different mAbαCD34 used for FACS analysis. The epitope which has provided an even performance is the HPCA-2(8G12 clone).

The CD34+ cells are now ready to be used. If the CD34+(lin+)cells are to be co-cultivated with thymic epithelial fragments or TEC monolayers, the absolute minimal stem cell concentration should be ~10,000 cells per fragment/monolayer. The cells will undergo a rapid expansion during the initial phase of the co-culture reflecting the expansion and terminal differentiation of the precommitted progenitors in the CD34+ population. At set intervals of the co-culture, prior to functional testing or phenotyping these "non-mononuclear" cells can be removed after cell harvesting by low density cell centrifugation with Ficoll-Hypaque.

COCULTURE OF CULTURED THYMIC EPITHELIAL FRAGMENTS AND CD34+ STEM CELLS

Place the Thymic Epithelial Fragments (TEF) in the bottom of the upper chamber of the transwell plate containing Iscove's/Ham's medium at a 1:1 ratio supplemented with 5% FCS, 0.4 µg/ml hydrocortisone (Calbiochem Behrig, La Jolla, Calif.), 11 ng/ml epidermal growth factor (Collaborative Research, Bedford, Mass.), $1\times10^{-10}$M cholera enterotoxin (Sigma), 5 µg/ml insulin (Sigma), $1.8\times10^{-4}$ g/ml sodium pyruvate, 50 µg/ml gentamycin.

The TEF media should be changed every 4–5 days until about 48 hours prior to the addition of stem cells. Prior to initiating the coculture phase by the addition of purified stem cells the media should be mixed 1.1 with the coculture type media in order to wean the TEF to the lymphocyte type coculture media which has less serum and reduced hydrocortisone. (Coculture Media: Iscove's/Ham's medium at a 1:1 ratio containing 5% FCS, 10% HL-1 serum free media (Ventrex), 11 ng/ml epidermal growth factor (Collaborative Research), and 25 U/ml of IL-2 at 37 C. in a 5% $CO_2$ atmosphere)

At the time the purified stem cells are ready to be added to the thymic fragments the TEF media should be completely aspirated from the upper and lower chambers of the transwell and coculture media should be added to the capacity of the outer well and to the halfway point of the inner well. The stem cells are then seeded to the upper well of the transwells containing the TEF fragments at a concentration of between 10,000 and 100,000 CD34+CD38− stem cells per fragment (depending on the lineage status). It has been noted by single cell sorting and clonal analysis that the pro-T subpopulation in bone marrow CD34+ cells ~7%, a limiting dilution series set up in the lab estimates a minimum of 20,000 stem cells per fragment (depends on stem cell source and degree of CD38 depletion). The TEF which are being cocultured with the purified stem cells should be checked periodically under the microscope for CD34+ cell expansion (to precommitted lines) and for assessing whether a portion of the cells are tracking to the thymic fragments. The epithelial skirt or monolayer which formed around the fragment during the TEF phase of culture should have several empty thymic nurse cell (TE-4 type cells) in the skirt, these may begin to show signs of new cells entering them after the coculture phase is established.

The following Examples, given by way of illustration only and not by of limitation, will provide a clear understanding of the manner in which the invention can be performed.

EXAMPLE 1
CULTURE OF BOTH ALLOGENEIC AND HIV INFECTED THYMIC EPITHELIAL FRAGMENTS

Allogeneic and HIV infected thymic epithelial fragments were cultured in vitro as described above. The thymic epithelial fragment cultures were analyzed for their morphological characteristics and integrity as tissue fragment cultures.

Morphological Assessment Thymus Tissue. Thymus was obtained from children undergoing corrective cardiac surgery, who have portions of their thymus removed as part of their surgical process. This process was approved by the St. Louis University Health Sciences Center Institutional Review Board, and informed consent was obtained from the subjects' parents.

HIV thymus was available for evaluation from three children with AIDS who were infected either in utero or during the newborn period. Each thymus was small and notably dysplastic. Structurally there were signs of significant stromal dysgenesis throughout the tissue. The capsular area was thickened with discontinuous patches of subcapsular tissue and effacement of the cortical epithelium. There was a prominent hyaline change with fatty infiltration throughout the tissue. The lobular architecture was collapsed and depleted of lymphocytes. Corticomedullary differentiation could not be appreciated. Hassal's corpuscles were absent.

Immunohistochemical localization of CD34+ stem cells by laser confocal imaging.

In an effort to further define the thymic stromal damage induced by HIV, a detailed histologic study was performed using laser scanning confocal microscopy (LSCM). Generation of reconstructed three-dimensional images with viewing of stereo images, orthogonal-Z sections and animated rotational scanning allowed through tissue viewing of otherwise structurally compromised thymic tissue. LSCM was selected for imaging the labelled tissue sections because of its ability to record images with enhanced XY resolution, with multiple fluorophores, in addition to recording reflected or transmitted images to provide high resolution, detailed morphology. (J. Pawley. ed., Handbook of Biological Confocal Microscopy, 2nd Edition Plenum Press, 311–323 (1995))

Orthogonal Z sections were obtained from several fields of each specimen to allow three-dimensional image reconstruction, quantitative image analysis and micrograph reproduction. Both normal thymic tissue and thymic tissue obtained at autopsy from children with end stage HIV affected Cultured Thymic Epithelial Fragments were set up in parallel using dual chamber culture slides, which were maintained in coculture media with thymic conditioned medium and T cell conditioned media, prepared as previously described. (M. Ruiz, S. T. Roodman. J. D. Bouhasin, et al., T cell Differentiation of CD34+ Stem Cells From HIV Seropositive Hemophiliacs in Cultured Thymic Epithelial Fragments, Stem Cells 14, 132–145 (1996)) The conditioned media added as a 10% supplement served as a source of stem cell factor, I1-1β, I1-3, I1-7, TGFβ and GM-CSF (determined by immunoblot analysis-data not shown). Small fragments of tissue were placed in chamber slides (Nunc), and stained with a panel of different mAb at optimal concentrations after set intervals of culture. Monoclonal antibodies, in addition to the above, included: TE-3, TE-4, CDR2 (a kind gift provided by Dr. Richard Hong); HIV protease (Molecular Probes); and CK-5 (anti-human keratins 8, 18 antibody; Sigma) and V-9 (anti-human vimentin antibody; Dako). Appropriate isotype fluorochrome conjugated secondary antibodies included goat a mouse F(ab) $_2$IgG or IgM conjugated to phycoerythrin (Tago), and rabbit α mouse F(ab)$_2$ IgG conjugated to FITC (Sigma).

Micrographs of tissue samples were obtained with a Zeiss LSM 410 scanning laser confocal microscope system built around a Zeiss 135 Axiovert inverted microscope. This particular system employs three photomultiplier tube (PMT) detectors, any two of which could be used for simultaneous recording of dual fluorescence labels at two different wave lengths or for simultaneously collecting one fluorescence label image and one reflection image. The third PMT was used for simultaneously imaging the nonconfocal transmission image of the same along with the two other PMT channels and for separately recording a fluorescence image of a third fluorophore. An Omnicron argon/krypton dual gas laser set to emit the 488, 568, and/or 647 nm laser lines was engaged.

Fluorescence images of the FITC label were recorded using a 488 nm laser line, recording the image through a broad band pass emission filter of 510–540 nm. Phycoerythrin (PE) fluorophore images were obtained with a 575–640 nm. Per-CP fluorophore images were obtained with a 488 nm laser line, recording the image through a broad band pass emission filter of 670–810 nm. Appropriate dual laser line beam splitters were used when recording single fluorophore of dual fluorophore images. Brightness (PMT gain) and contrast (PMT DC offset) were set on appropriate positive control samples to obtain a full 8 bit grey scale rendering of each image.

In the case of sample versus control comparisons, the brightness and gain settings for the sample were held fixed for the subsequent recording of the image of the control sample. Microscope images were obtained using either a Zeiss 63X oil/NA=1.25 Neofluor objective or a Zeiss 40X Achroplan 0.60 Korr Ph2 objective. The pinhole of the confocal system was adjusted for maximal spatial resolution which for the 63X objective yielded an ultimate XY resolution of ~0.20 µm in the XY plane. Simultaneous recording of either single or dual fluorescence labeled images plus epireflection images were primarily utilized in this study. Digital image data (with some files exceeding 14 Mb in size) were stored on a 256 Mb MO drive. Three-dimensional image reconstruction from Z sections was performed with the software provided by Zeiss for the LSM 410 system.

Normal thymic tissue, evaluated using LSCM with tissue sections of 50µ (maximum of 100µ), were able to be visualized without structural distortion. Transitional areas were sought in an effort to orient the optical dissection. In an effort to visualize detailed cell morphology underlying the fluorescence images epireflection images were simultaneously recorded with the fluorescence images. With regard to the stem cell compartment of the thymus, the subcapsular areas in normal thymic tissue contained liberal numbers of CD34+ stem cells.

The HIV affected thymic tissue contained a predominantly thickened and reticular subcapsular cortex. The discontinuous patches of subcapsular cortical tissue contained scant patches of TE-4+ TEC and predominant clusters of stem cells. Amid these dense tufts of stem cells there were clusters of cells with fused cell membranes between adjacent cells. No multinucleated giant cells were appreciated. The cortical areas of the HIV tissues were effaced and devoid of both lymphocytes and epithelial cells. In addition, a distinct loss of Hassall's corpuscles was observed. Both NK and B cells were present in the HIV tissue in a slightly higher proportion than that appreciated for normal thymic tissue; however, this may be reflective of the significant T cell depletion present.

With regard to the thymic stroma, the subcapsular area of the normal thymus contained modest numbers of TE-4+ TEC. The cortical stromal tissues predominantly stained with TE-3 and CDR2. Lymphocytes were present throughout the cortical and medullary regions. Corticomedullary differentiation was easily appreciated as was the presence of Hassall's corpuscles.

Vimentin and Keratin Immunostaining. The epithelial and mesenchymal cellular components of thymic tissue were further characterized by vimentin immunostaining of cells in the stromal compartment, and keratin immunostaining of epithelial cells throughout the tissue. Dissolution of morphological architecture was the major finding in the HIV tissue compared with matched normal tissue.

The normal thymus is capable of maintaining both a pro-T (multilineage) and a pre-T (committed) CD34+ stem cell population. (H. Spits, L. Lanier, J. Phillips, Development of Human T and Natural Killer Cells, Blood 85, 2654–2670 (1995)) The integrity of the thymic epithelial microenvironment (ME) is dependent on a continual supply of stem cells. The pro-T cell population provides not only lymphocyte precursors but also dendritic cells which support the stromal cell populations and present antigen to developing lymphocytes. Thymic stromal dysgenesis has been noted when there are alterations induced in the ingressing stem cell populations. An example of the inductive ME provided by stem cells has recently been described by Hollander et al. in transgenic mice defective in the CD3ε chain. (G. Hollander, B. Wang, A. Nichogiannopoulou, et al., Developmental Control Point in Induction of Thymic Cortex Regulated by a Subpopulation of Prothymocytes, Nature 373, 350–353 (1995)) In this murine model the thymic architecture lacked distinct cortical and medullary compartments. Failure to form even a rudimentary corticomedullary ME in these CD3ε–/–tg is presumably due to a change in soluble cytokines or direct signals transmitted to thymic epithelial cells by transiting stem cells. Normal thymopoiesis could only be reconstituted by the transplantation of wild type stem cells in fetal CD3ε–/–tg thymic stroma, further indicating a defined developmental window for inducing corticomedullary differentiation. A broader developmental window may exist in humans, as reflected in severe combined Immuno-Deficiency Syndrome (SCIDS). Long term T cell reconstitution has been achieved in SCIDS patients transplanted with normal bone marrow stem cells. (C. Nezelof, Invited Review, Thymic Pathology in Primary and Secondary Immunodeficiencies, Histopath 21, 499–511 (1992).)

EXAMPLE 2
T CELL DIFFERENTIATION OF CD34+ STEM CELLS FROM NORMAL VOLUNTEERS IN CULTURED THYMIC EPITHELIAL FRAGMENTS FROM HIV INFECTED INDIVIDUALS AND NORMAL VOLUNTEERS

Allogenic and HIV infected thymic epithelial fragments were cocultured in the process described above. The process and progress of these cocultures were analyzed as follows.

Stem cell migration visualized by time-lapse videomicroscopy.

CD34+ stem cell migration was videotaped on a Sanyo SVHS 4-head Time-Lapse Video Cassette Recorder over a 48–96 hour period using a Zeiss Axiovert 135 microscope equipped with a Focht's environmental chamber and DIC optics. An aliquot of the enriched CD34+ stem cells was submitted for Fluorescence Activated Cell Sorting (FACS) analysis both prior to and subsequent to their addition to the TEC monolayer. Video stills were printed on a Sony Mavigraph UP-5200MD color video printer.

Although significant T cell depletion was present in all HIV thymi examined, CD34+ stem cells were present in the subcapsular regions of the tissue. The presence of bone marrow derived stem cells suggests the capacity of the bone marrow-microenvironment to export pro-T cells, and their ability to home in significant numbers and marginate into the thymus remain functional despite significant thymic end organ damage. Chemotaxis and chemokinesis of CD34+ stem cells is mediated by soluble factors. Thymic hormones such as thymotaxin, thymulin and thymopoietins have been implicated in mediating migration from the bone marrow and immigration into the thymus.

Chemokinesis of CD34+ stem cells was evaluated and recorded using time lapse videomicroscopy. Baseline studies were performed using normal CD34+ stem cells migrating toward a T cell depleted normal donor derived thymic epithelial cell monolayer. Analysis of the cells obtained after culture on the thymic epithelial monolayer by flow cytometry verified the acquisition of early T cell differentiation markers. T cell depleted thymic epithelial cell monolayers derived from an HIV host were capable of attracting normal CD34+ stem cells and maintained a small percentage of the CD34+ phenotype over the recorded period. Analysis of cells obtained after culture on the HIV donor derived thymic epithelial cell monolayer failed to show acquisition of CD3, CD4, or CD8 T cell differentiation markers.

DETECTION OF T CELL PHENOTYPES PRESENT IN HIV THYMUS

T cell surface phenotypes of thymocytes freshly isolated from the processed tissue and later from thymocytes harvested after the stem cell coculture were determined by staining with a panel of monoclonal antibodies (mAb) conjugated with different fluorochromes and analyzed by flow cytometry. Cells were aspirated from the culture wells, washed, resuspended in RPMI containing 5% Fetal Calf Serum (FCS) then subjected to Ficoll-Hypaque density centrifugation to remove dead cells. The mononuclear cells isolated from the interface were washed, resuspended in PBS containing 10% FCS and mixed with optimal concentrations of mAb. Ten thousand cells were stained with mAb and 5000 events recorded for analysis. Monoclonal antibodies used included: CD45, CD14, CD34, CD3, CD4, CD8, CD16, CD38, CD56, CD20, TCR$\alpha\beta$ and TCT$\gamma\delta$ obtained from Becton Dickinson. Negative controls (murine $IgG_1$ FITC/PE/PerCP; Becton Dickinson) emitted only a small percent of positive fluorescence and were used to set the positive gate. The lymphocyte region was selected using CD45 gating. Combinations of mAbs were used to identify immature thymocytes, such as double positive (CD3–CD4+CD8+) and triple positive (CD3+CD4+CD8+) thymocytes, and mature CD3+CD4+CD8– or CD3+CD4–CD8+ T cells. Fluorescein (FITC), phycoerythrin (PE) and peridinin chlorophyll protein (Per-CP) fluorescence was measured using the appropriate bandpass filters in a FACScan flow cytometer (Bectin-Dickinson). The analysis of three color populations was performed using the WinList program (Verity). In order to verify the cells harvested from the coculture were derived from the stem cell donor, CD34+CD38–stem cells were pre-labeled with 5-(and-6)-(((4-chloromethyl)bensoyl) amino)tetra-methyl-rhodamine (CMTMR; Molecular Probes, Inc.) prior to CTEF coculture. CMTMR is retained in living cells through multiple cell divisions and is not transferred to adjacent cells. The fluorochrome can be detected using standard cytometry or fluorescence microscopy with excitation at 480 nm and omission at 580–610 nm bandpass; however, the use of the cell tracker probe CMTMR precludes the use of double and triple labeling. Therefore a second series was examined in which the stem cells were not prelabelled with CMTMR in order to assess the phenotype of the harvested cells using triple labeling.

Thymocytes freshly isolated from both normal thymic tissue and HIV affected thymus tissue were analyzed by flow cytometry. The thymocytes derived from the HIV donors were significantly T cell depleted. Both CD34+ stem cells and CD3–CD4–CD8-triple negative thymocytes were present as were small populations of CD3+CD8+, NK cells and B cells. The proportions of double and triple positive thymocyte subpopulations were significantly decreased, as follows:

TABLE 1

Phenotypic analysis of freshly isolated thymocytes show an arrest of T cell differentiation in HIV thymus.

Mean Percent Distribution

| PHENOTYPE: | Normal Thymus n = 6 | HIV Thymus n = 3 |
|---|---|---|
| CD34+ | 1.8 | 4.52 |
| CD3–CD4–CD8–(TN) | 6.88 | 58.1 |
| CD3–CD4+CD8+(DP) | 34.25 | 0.69 |
| CD3+CD4+CD8+(TP) | 10.46 | 7.3 |
| CD3+CD4+(SP) | 3.12 | 1.53 |
| CD3+CD8+(SP) | 12.23 | 5.2 |
| CD3+TCR$\alpha\beta$ | 23.57 | 5.23 |
| CD3+TCR$\gamma\delta$ | 0.32 | 0.11 |

In vitro thymopoiesis of CD34+CD38– stem cells in HIV Cultured Thymic Epithelial Fragments.

Enriched CD34+CD38– stem cells isolated from normal bone marrow were cocultured with thymic epithelial fragments from either normal children or children with AIDS. T cell surface phenotypes of the differentiated stem cells was determined by reacting monoclonal antibodies conjugated with either fluoresein, phycoerythrin, and peridinin chlorophyll protein and then analyzed by flow cytometry (Fluorescence Activated Cell Sorting FACS) as described above.

Combinations of monoclonal antibodies were used to identify immature thymocytes, such as double-positive (CD3–CD4+CD8+) and triple positive (CD3+CD4+CD8+) thymocytes, and mature CD3+CD4+CD8– and CD3+CD4–CD8+ T cells. Mononuclear cells and Cultured Thymic Epithelial Fragments were aspirated from the culture wells, washed, resuspended in Phosphate buffered saline containing 10% Fetal calf serum, and then subjected to Ficoll-Hypaque density centrifugation to remove dead cells. The mononuclear cells at the interface were washed twice, resuspended in phosphate buffered saline containing 10% fetal calf serum. One to $5\times10^4$ cells were mixed with optimal concentrations of monoclonal antibodies and analyzed by cytofluorometric analysis using a FACScan flow cytometer (Becton Dickinson). Negative controls (murine IgG1-FITC; IgG1-Per-CP; Becton Dickinson) emitted only a small percent of positive fluorescence and were used to set the positive gate. The lymphocyte region was selected using CD45 gating. Analysis of three-color populations was performed using the WinList program (Verity).

In order to ensure that the Stem Cell/Cultured Thymic Epithelial Fragment T cells originated from the donor CD34+ stem cell population, three different methods were employed. In some cultures, Human Leucocyte-Antigens (HL-A) phenotype analysis of the thymocytes obtained from the stem cell/Cultured Thymic Epithelial Fragment coculture was determined using standard serological HL-A typing techniques. This was then compared to the stem cell and the thymus donor HL-A phenotype. In other experiments, CD34+CD38+ Stem Cells were labeled with 5-(and -6)-((4-chloromethyl)benzoyl)amino) tetramethylrhodamine (CMTMR; Molecular Probes, Inc.) prior to coculture with the Cultured Thymic Epithelial Fragment. CMTMR is retained in living cells through several generations and is not transferred to adjacent cells. Fluorescence of CMTMR within CD2+ and CD4+ thymocytes (FITC) from the stem cell/Cultured Thymic Epithelial Fragment cocultures was measured at 585 nm by flow cytometry, confirming stem cell origin of the thymocytes.

The ability of the thymic epithelia derived from an HIV+ host to support thymopoiesis was markedly diminished compared to normal controls. There were decreased cellular differentiation, 13,000 cells/Cultured Thymic Epithelial Fragments in HIV compared to 58,000 cells/Cultured Thymic Epithelial Fragments in normal controls (p<0.01).

Examination of thymocytes and T cell populations by flow cytometry revealed markedly abnormal differentiation and maturation in the HIV thymic organ cultures. This was most evident in CD4+ bearing cells, as shown in Table 2.

TABLE 2

Abnormal thymopoiesis of CD34+CD38– stem cells in HIV+ cultured thymic epithelial fragments.

| PHENOTYPE: | Normal Thymus | HIV Thymus | P value |
|---|---|---|---|
| cells/CTEF | 58604 ± 8481 | 13000 ± 5333 | 0.01 |
| CD3+ | 75 ± 11 | 36 ± 10 | 0.03 |
| CD4+ | 52 ± 19 | 20 ± 6 | 0.05 |
| CD8+ | 67 ± 9 | 64 ± 20 | |

TABLE 2-continued

Abnormal thymopoiesis of CD34+CD38– stem cells in HIV+ cultured thymic epithelial fragments.

| PHENOTYPE: | Normal Thymus | HIV Thymus | P value |
|---|---|---|---|
| CD3–CD4–CD8–(TN) | 1.5 ± 0.4 | 28 ± 20 | |
| CD3–CD4+CD8+(DP) | 24 ± 11 | 9 ± 4 | 0.05 |
| CD3+CD4+CD8+(TP) | 21 ± 13 | 12 ± 6 | |
| CD3+CD4+(SP) | 28 ± 9 | 4 ± 4 | 0.02 |
| CD3+CD8+(SP) | 25 ± 9 | 19 ± 14 | |
| CD3+TCRαβ | 84 ± 5 | 81 | |
| CD3+TCRγδ | 1.0 ± 0.5 | 0.5 | |

P value using Student's t-test.

Abnormal thymocyte populations were manifested by decreased expression of CD3+ cells in HIV versus controls, 36% versus 75% (p<0.03), respectively; and in CD4+ cells, 20% versus 52% (p<0.05), respectively (Table 2). Furthermore, there were increased triple negative CD3–CD4–CD8–thymocytes in the HIV thymus compared to normal, 28% versus 1.5%. Subpopulations of CD4+ bearing thymocytes were also decreased in the HIV thymic organ culture. Expression in normal vs HIV thymus, respectively, of: double positive CD4+CD8+ thymocytes (24% versus 9%, p=0.053); and triple positive CD3+CD4+CD8+ thymocytes (21% versus 12%, p<0.01); and single positive mature CD4+ T cells (28% versus 4%, p=0.011) were markedly decreased in the HIV thymic epithelial cocultures. The acquisition of CD8 and TCRαβ were normal in the HIV+ thymus, suggesting that HIV+ thymic epithelia can support CD8+ lineage development.

The thymic tissues studies in this series had significant end organ damage, but still allowed several important observations. Migration studies show that HIV affected thymic tissue is capable of attracting CD34+ stem cells in vitro. During HIV infection the migration of stem cells to the thymus in vivo is supported by the demonstration of CD34+ stem cells in the subcapsular cortical areas of HIV+ thymus. The stem cells present in the subcapsular cortical areas of the HIV thymus can be infected by HIV, as evidenced by their ability to cleave an HIV specific protease probe and develop distinct changes in cell morphology (syncytia). Therefore, the stem cell compartment of the thymus which is responsible for maintaining both the integrity of the lymphoid compartment and for providing signals for the regeneration of the epithelial compartment is damaged during infection with HIV. There are significant alterations in the thymic stromal and supporting cell populations present in the HIV thymus. The thymic stromal stem cells present in epithelial guirlandes are able to differentiate in vitro but the functional status of these cells remains to be determined. Our data suggest that the HIV thymus does support thymopoiesis; however, it is compromised both in rate and in the diversity of thymocyte subpopulations.

EXAMPLE 3

T CELL DIFFERENTIATION OF CD34+ STEM CELLS FROM HIV SEROPOSITIVE HEMOPHILIACS IN CULTURED THYMIC EPITHELIAL FRAGMENTS FROM NORMAL VOLUNTEERS:

Stem Cells were obtained from bone marrow aspirates of HIV-infected hemophiliacs. Bone marrow was collected in heparinized tubes, diluted in normal saline, and the nucleated cells obtained by Ficoll-Hypaque density centrifugation. The purified stem cells were cocultured with cultured thymic epithelial fragments as described above and analyzed as follows.

The percentage of CD34+ stem cells recovered from the bone marrow mononuclear cell population was increased approximately 10-fold in the HIV-seropositive hemophiliacs compared to the values reported for normal individuals (LWMM Terstappen, S. Huang, P. M. Safford, et al., *Sequential Generations of Hematopoietic Colonies Derived from Single Nonlineage-Committed CD34+CD38– Progenitor Cells*, Blood 77, 1217–1218 (1991)). This increased CD34+ stem cell population may reflect a depletion of T cells with a relative increased percentage of stem cells in the bone marrow. Our study indicates that HIV-infected hemophiliacs have adequate numbers of bone marrow stem cells which were capable of differentiating into functional T cells in vitro, see below.

TABLE 3

Peak T cell differentiation of CD34+ Stem Cells from HIV seropositive hemophiliacs in CTEF cocultures.

| | SC-CTEF T Cell Phenotypes, % | | | | | | | | |
|---|---|---|---|---|---|---|---|---|---|
| Patients | CD34 | CD44 | CD7 | CD2 | CD3 | CD4 | CD5 | TCRαB | TCRγδ |
| 1 | 2 | 72 | nd | 59 | 41 | nd | nd | 19 | 2 |
| 3 | nd | nd | nd | 47 | 41 | 30 | nd | 10 | nd |
| 4 | 24 | 21 | 34 | 21 | 33 | 25 | 23 | 40 | 22 |
| 5 | 3 | nd | 72 | 81 | 78 | nd | nd | 23 | nd |
| 6 | 3 | nd | 95 | 96 | 93 | 59 | 31 | 87 | 1 |
| 7 | 9 | nd | 70 | 64 | 83 | 47 | 11 | 52 | 23 |
| 8 | 4 | nd | 85 | 74 | 93 | 55 | 22 | 83 | 11 |
| 9 | 8 | nd | 20 | 80 | 52 | 14 | 7 | 14 | 4 |
| 10 | nd | 15 | 74 | 63 | 86 | 36 | 15 | 59 | 4 |
| 11 | 5 | nd | 19 | 12 | 90 | 15 | 4 | 37 | 2 |
| 12 | 4 | nd | 14 | 15 | 27 | 3 | 3 | 4 | nd |
| Number | 8 | 4 | 9 | 11 | 11 | 9 | 8 | 11 | 8 |
| Mean ± SD | 7 ± 6 | 28 ± 26 | 54 ± 30 | 56 ± 27 | 65 ± 25 | 32 ± 18 | 15 ± 9 | 39 ± 27 | 9 ± 9 |

Abbreviation: nd = not done

Though CTEF were seeded with stem cells which were greater than 95% CD34+, the CD34+ cells represented only a small fraction of the cells after coculture in the thymic epithelial fragments. The results indicate, however, that enriched stem cell populations from bone marrow of HIV infected hemophiliacs were capable of differentiating into T cells when cocultured in a normal allogeneic thymic environment.

In order to ensure that the Stem Cell/Cultured Thymic Epithelial Fragment T cells originated from the donor CD34+ stem cell population. Human Leucocyte-Antigen (HL-A) phenotype analysis of the thymocytes obtained from the stem cell/Cultured Thymic Epithelial Fragment coculture was determined using standard serological HL-A typing techniques. This was then compared to the stem cell and the thymus donor HL-A phenotype. HL-A phenotype of the differentiated T cells was the same as the stem cell donor and disparate from the CTEF donor.

In a similar manner. Cultured Thymic Epithelial Fragments may be cocultured with genetically modified stem cells. i.e., stem cells which have been modified to contain potentially HIV protective genes. The coculture of genetically modified stem cells permits assessment of the ability of the cultured thymic epithelial fragment to differentiate the modified stem cells to full immunocompetence.

EXAMPLE 4
LYMPHOPROLIFERATIVE RESPONSES TO PHYTOHEMAGGLUTININ (PHA)

Differentiated T cells from the culture of stem cells and thymic epithelial fragments have acquired the capacity of mature T cells to proliferate when nonspecifically stimulated with PhytoHemAgglutinin (PHA). T cell proliferation to PHA stimulation is dependent on antigen-presenting cells (APCs), but is not HL-A-restricted. Parallel studies were performed using APCs of each stem cell and thymus donor to determine whether the newly differentiated T cells cooperated optimally with APCs of the stem cell or thymic donors. B cells, transformed with Epstein Barr virus (EBV-B), served as APCs as previously described (AP Knutsen, KR Mueller, AD Levin, et al., Characterization of AsP fl CD4+ Cell Lines in Allergic Bronchopulmonary Aspergillosis. J. Allergy Clin. Immunology 94, 215–221 (1994); A. P. Knutsen, J. D. Bouhasin, J. H. Joist. et al., Decrease of CD4 Cells and Function in HIV Seropositive Hemophiliacs in a Longitudinal Study, Ann Allergy 63, 189–194 (1989); A. P. Knutsen, and K. R. Mueller, T-cell Cytotoxicity in Cystic Fibrosis: Relationship to Pulmonary Status, Int Arch Allergy Appl Immunol 93, 54–58 (1990)). Five×10$^5$ CTEF T cells cocultured with 20% B cells derived from either the stem cell or thymic donor were stimulated with PHA for three days at 37° C. in a 5% $CO_2$ humidified atmosphere (A. P. Knutsen, J. D. Bouhasin, J. H. Joist, et al., Decrease of CD4 Cells and Function in HIV Seropositive Hemophiliacs in a Longitudinal Study. Ann Allergy 63, 189–194 (1989); A. P. Knutsen, and K. R. Mueller, T-cell Cytotoxicity in Cystic Fibrosis: Relationship to Pulmonary Status, Int Arch Allergy Appl Immunol 93, 54–58 (1990)). Tritiated thymidine 1 µCi (ICN) was added to each well for the final 18 hours of culture. The cultures were harvested onto glass filter paper and the tritiated-thymidine incorporated into DNA was counted in a Beckman beta scintillation counter. Data were expressed as geometric mean net counts per minute of stimulated (E) minus unstimulated (C) cultures and as stimulation index (SI) calculated as E divided by C. The results were as follows:

TABLE 4

Lymphoproliferative responses to PHA stimulation by T cells obtained from Stem Cells from HIV-seropositive hemophiliacs' CTEF cultures.

| Patients | SC-CTEF T Cells + SC B cells | | | SC-CTEF T Cells + CTEF B cells | | |
|---|---|---|---|---|---|---|
| | Media, cpm | Net cpm | SI | Media, cpm | Net cpm | SI |
| 1 | 5810 | 42092 | 8.2 | 1976 | 4826 | 3.4 |
| 4 | 1976 | 4826 | 3.4 | | | |
| 5 | 966 | 5069 | 6.2 | | | |
| 6 | 4882 | 52985 | 11.9 | 3319 | 2645 | 1.8 |
| 7 | 1482 | 18762 | 13.7 | 4071 | 7100 | 2.7 |
| 8 | 2057 | 5209 | 26.3 | 674 | 217 | 1.3 |
| 9 | 2238 | 73115 | 33.7 | | | |
| 10 | 1043 | 3289 | 4.2 | 632 | −86 | 0.9 |
| 11 | 917 | 3982 | 5.3 | | | |
| 12 | 1025 | 8130 | 8.9 | 16256 | 46696 | 3.9 |
| Mean x/+SE | 1803x/+1.2 | 11530x/+1.4 | 9.3x/+1.3 | 2403x/+1.6 | 1553x/+4.7 | 3.1x/+1.6 |

As shown in Table 4, T cells obtained from SC of HIV+ hemophiliacs which had been cocultured with CTEFs were assayed at multiple times for PHA stimulation in order to obtain the period of maximal stimulation. The time course of optimal PHA lymphoproliferative responses paralleled expression of mature T cell surface molecules. In paired experiments, responses to PHA stimulation were observed when APCs derived from either the stem cell or thymic donors were used. However, maximal response to PHA stimulation was significantly increased with APC of the stem cell donors compared to APC of thymus donors, geometric mean of 11530x/+1.4 (SI 9.3x/+1.3) versus 1553 x/+4.7 net cpm (SI 3.1x/+1.6) (p<0.03) (Table 4). To date no other model has demonstrated functional immunocompetent T cells, but have referred phenotypic maturity with immunocompetence.

EXAMPLE 5
ANALYSIS OF SC-CTEF DERIVED T CELL TOLERANCE TO THYMIC HUMAN LEUCOCYTE ANTIGENS (HL-A's)

To evaluate whether the SC-CTEF-derived T cells were tolerant to allogeneic thymic HL-A antigens, a one-way Mixed Lymphocyte Culture (MLC) to EBV-B cells from the thymic donor as the target cells was performed (A. P. Knutsen, K. R. Mueller, A. D. Levin, et al., Characterization of Asp fl CD4+ Cell Lines in Allergic Bronchopulmonary Aspergillosis, J. Allergy Clin. Immunology 94, 215–221 (1994)). Previous studies in mice and humans have demonstrated that T cells produced in the allogeneic thymus were tolerant to thymic HL-A antigens. As a positive control, MLC reactivity to pooled B cells was simultaneously performed. CTEF T cells (0.5×10$^5$ cells) were cultured with mitomycin C-treated EBV-B cells (0.5×10$^5$ cells) obtained from the stem cell, thymic or pooled B cell donors for six days at 37° C. in a 5% $CO_2$ atmosphere. Tritiated thymidine 1 µCi (ICN) was added to each well for the final 18 hours of culture. The cultures were harvested onto glass filter paper and the tritiated thymidine incorporated into DNA was counted in a Beckman beta scintillation counter. The results were as follows:

In addition, the chimeric SC-CTEF T cells also did not respond to stimulation with B cells of either stem cell donor

TABLE 5

Mixed Lymphocyte Culture reactivity by T cells obtained from CD34+ Stem Cells from HIV-seropositive hemophiliacs in CTEF cocultures. Responding SC-CTEF T cells stimulated with:

| Patients | T alone cpm | Pooled B Cells | | SC B cells | | CTEF B cells | |
|---|---|---|---|---|---|---|---|
| | | Net cpm | SI | Net cpm | SI | Net cpm | SI |
| 1  | 569     | 9699     | 18.0      | 2424    | 5.3       | 1187    | 3.1 |
| 4  | 619     | 5445     | 9.8       | 6675    | 11.8      | 2206    | 4.6 |
| 6  | 946     | 3449     | 4.6       | −85     | 0.9       | −212    | 0.8 |
| 7  | 161     | 385      | 3.4       | 224     | 2.4       | 101     | 1.6 |
| 8  | 3199    | 31122    | 10.7      | −1963   | 0.4       | −2173   | 0.3 |
| 9  | 418     | 5090     | 13.2      | 3579    | 9.6       | 53      | 1.1 |
| 10 | 2227    | 6874     | 4.1       | 8200    | 4.7       | 10      | 1.0 |
| 11 | 1463    | 63657    | 44.5      | 36      | 1.0       | −746    | 0.5 |
| 12 | 1153    | 2391     | 3.1       | 1920    | 2.7       | 819     | 1.7 |
| *  | 864x/÷1.3 | 6096x/÷1.6 | 8.5x/÷1.3 | 269x/÷3.1 | 2.7x/÷1.4 | 36x/÷2.7 | 1.2x/÷1.3 |

*mean x/÷ SE

As seen in Table 5, T cells obtained from the stem cell and thymic epithelial cocultures responded to allogeneic HL-A antigens of pooled B cells, geometric mean net cpm of 6096x/÷1.6 (SI 8.5x/÷1.3). In paired cultures, these T cells failed to respond to HL-A antigens of B cells from the thymus donor, geometric mean net cpm of 36x/÷2.7 (SI 1.2x/÷1.3) ($p<0.05$) and had reduced reactivity to HL-A antigens from B cells of the stem cell donor, geometric mean net cpm of 269 x/÷3.1 (SI 2.7x/÷1.4) ($p<0.05$). These SC-CTEF T cells demonstrated some self-alloreactivity to stem cell HL-A antigens in four of nine patients. Furthermore, in three patients who were tested at a later time point, MLC response to B cells of the stem cell donor subsequently disappeared upon further duration of the SC-CTEF coculture (data not shown). These studies suggested that SCs gave rise not only to T cells but also to accessory cells populating the thymus which contributed to tolerance.

To further evaluate this hypothesis, two HL-A disparate donor populations of SCs were cultured simultaneously in the same thymic epithelial fragment culture and MLC reactivity was then examined toward APCs from each stem cell donor. In these experiments, SC-CTEF T cells responded to stimulation with HL-A antigens of the pool B cells and did not respond to the thymus donor B cells as expected, as shown in Table 6 below.

in six of eight experiments. These studies suggested that HL-A tolerance was being induced by cells originating from the stem cell donors as well as the thymic epithelial HL-A antigens.

Differentiated T cells from the stem cell and thymic epithelia fragment cocultures were tolerant of thymic HL-A antigens as expected. This further supports the observations that graft rejection was not mediated by newly differentiated T cells from the thymic graft (S. A. Danner, H. J. Schuurman, J. M. A. Lange, et al., Implantation of cultured thymic epithelial fragments in patients with acquired immunodeficiency syndrome, Arch Intern Med. 146, 1133–1136 (1986); J. M. Dwyer, C. C. Wood, J McNamara, et al., Transplantation of thymic tissue into patients with AIDS, Arch Intern Med 147, 513–517 (1987)). Our studies also suggested that HL-A restriction or tolerance was also mediated via bone marrow-derived accessory cells. Thymocytes and accessory cells, such as dendritic cells, were largely eliminated by 2'-deoxyguanosine treatment, prior to seeding with SC; yet differentiated T cells generated were tolerant to B cells of the thymic donor. These T cells were found to be tolerant to thymic HL-A antigens by clonal anergy and to self-antigens by clonal deletion. Though the mechanism of tolerance was not investigated in our studies, SC-CTEF T cells were observed to be tolerant of thymic HL-A antigens and demonstrated reduced MLC reactivity to self-antigens.

TABLE 6

Mixed Lymphocyte Culture reactivity by chimeric T cells obtained from two CD34+ Stem Cell donors cultured in the same thymic epithelial fragment. Responding SC-CTEF T cells stimulated with:

| Patients | T alone cpm | Pooled B Cells | | SC#1 B cells | | SC#2 B cells | | CTEF B cells | |
|---|---|---|---|---|---|---|---|---|---|
| | | Net cpm | SI | Net cpm | SI | Net cpm | SI | Net cpm | SI |
| 1 | 1731  | 21213 | 13.3 | 9736  | 6.6 | 9552  | 6.5 | −526  | 0.7 |
| 2 | 12674 | 26610 | 3.1  | −4416 | 0.7 | −6593 | 0.5 | −9342 | 0.3 |
| 3 | 3645  | 11599 | 4.2  | −2479 | 0.3 | −930  | 0.7 | −742  | 0.8 |
| 4 | 1702  | 35896 | 22.1 | 3440  | 3.0 | 2499  | 2.5 |       |     |
| 5 | 4354  | 7390  | 2.7  | −1268 | 0.7 | −3057 | 0.3 | −3575 | 0.2 |
| 6 | 3951  | 6471  | 2.6  | 43    | 1.0 | −551  | 0.9 | −175  | 1.0 |
| 7 | 318   | 1092  | 4.4  | 545   | 2.7 | 552   | 2.7 | 403   | 2.3 |
| 8 | 4278  | 39529 | 10.2 | −2154 | 0.5 | −1890 | 0.6 | −1831 | 0.6 |

Furthermore, tolerance was observed to both stem cell donor HL-A antigens when chimeric SC cultures were performed.

Although preferred embodiments of the invention have been described in the foregoing Specification, it is to be understood that the invention is not limited to the exact embodiments disclosed or to the exact details of operation or exact methods or procedures shown and described, since the invention is capable of numerous modifications, rearrangements, and substitutions of procedures without departing from the spirit or scope of the invention, as well readily be apparent to one skilled in the art, wherefore the present invention is to be understood as limited only by the full scope which can be legally accorded the appended claims.

I claim:

1. A process of coculturing Cultured Thymic Epithelial Fragments and bone-marrow derived stem cells whereby the stem cells are differentiated into immunocompetent T cells, comprising the following steps:

establishing cultured thymic epithelial fragment cultures by:

excising thymus tissue as a metabolic specimen avoiding mechanical pressure and heat cauterization and placing the tissue in chilled media, removing the thymic capsule from the excised thymic tissue, mincing the tissue into small fragments and agitating the fragments in complete media to wash out thymocytes, depleting thymocytes and hematopoietic cells including dendritic cells by incubating the fragments on sterile tissue rafts which are partially immersed in complete medium supplemented with 2'-deoxyguanosine, at about 37° C. in a partial $CO_2$ atmosphere, and culturing the T cell depleted fragments to optimize stromal viability in complete medium supplemented with hydrocortisone, epidermal growth factor, cholera enterotoxin, insulin, adenine, and sodium pyruvate, isolating CD34+CD38− stem cells by:

performing Ficoll-Hypaque density centrifugation to obtain nucleated bone marrow cells from bone marrow aspirates diluted in normal saline, depleting CD2+ lymphocytes by rosette formation with sheep Red Blood Cells treated with 2-amino-ethyl isothiouronium bromide, followed by a second Ficoll-Hypaque density centrifugation, removing non-CD34 cells by culture with monoclonal antibodies or immunomagnetic microbeads, followed by separation over a monoclonal antibody-coated panning flask or magnetic column, and coculturing the Cultured Thymic Epithelial Fragments and purified CD34+CD38− Stem Cells by:

seeding CD34+CD38− stem cells by infusion onto the surface of the Cultured Thymic Epithelial Fragments in transwell plates in Iscove's/Ham's medium containing IL-2 at about 37° C. in a partial $CO_2$ atmosphere until differentiated into mature T cells, replacing medium every few days, and isolating the differentiated T cells by aspirating the cells from the culture wells, washing, resuspending in saline, subjecting the cells to Ficoll-Hypaque density centrifugation to remove dead cells, washing the mononuclear cells, and resuspending the pure mononuclear cells in saline.

2. A process of coculturing Allogeneic Cultured Thymic Epithelial Fragments and bone-marrow derived stem cells from HIV seropositive patients whereby the stem cells are differentiated into immunocompetent T cells free of HIV infection, comprising the following steps:

establishing cultured thymic epithelial fragment cultures by:

excising thymus tissue as a metabolic specimen avoiding mechanical pressure and heat cauterization and placing the tissue in chilled media, removing the thymic capsule from the excised thymic tissue, mincing the tissue into small fragments and agitating the fragments in complete media to wash out thymocytes, depleting thymocytes and hematopoietic cells including dendritic cells by incubating the fragments on sterile tissue rafts which are partially immersed in complete medium supplemented with 2'-deoxyguanosine, at about 37° C. in a partial $CO_2$ atmosphere for at least seven days, and culturing the T cell depleted fragments to optimize stromal viability in complete medium supplemented with hydrocortisone, epidermal growth factor, cholera enterotoxin, insulin, adenine, and sodium pyruvate, isolating CD34+ stem cells from HIV seropositive patients by:

collecting bone marrow from aspirates in Heparinized tubes, performing Ficoll-Hypaque density centrifugation to obtain nucleated bone marrow cells from bone marrow aspirates diluted in normal saline, depleting CD2+ lymphocytes by rosette formation with sheep Red Blood Cells treated with 2-amino-ethyl isothiouronium bromide, followed by a second Ficoll-Hypaque density centrifugation, removing macrophage/monocytic cells by adherence on plastic Petri dishes, removing non-CD34 cells by culture with monoclonal antibodies or immunomagnetic microbeads, followed by separation over a monoclonal antibody-coated panning flask or magnetic column, and coculturing the Cultured Thymic Epithelial Fragments and purified CD34+CD38− Stem Cells by:

seeding a minimum of 5,000 lineage negative stem cells or 50,000 lineage committed stem cells by infusion onto the surface of the Cultured Thymic Epithelial Fragments in transwell plates in Iscove's/Ham's medium containing IL-2 at about 37° C. in a partial $CO_2$ atmosphere until differentiated into mature T cells, replacing medium every few days, and isolating the differentiated T cells by aspirating the cells from the culture wells, washing, resuspending in saline, subjecting the cells to Ficoll-Hypaque density centrifugation to remove dead cells, washing the mononuclear cells, and resuspending the pure mononuclear cells in saline.

3. A process whereby thymic microenvironmental performance (i.e. thymopoiesis) may be evaluated comprising the step of carrying out the process of claim 1 or claim 2 in the presence of a compound proposed to be used for HIV therapy to determine if the stem cell differentiation is inhibited or otherwise altered in the presence of said compound.

4. A process of expanding and differentiating bone marrow-derived stem cells into immunocompetent T cells comprising the step of coculturing the stem cells in an in vitro Cultured Thymic Epithelial Fragment 3-D microenvironment which comprises more than an Thymic Epithelial Cell Monolayer.

* * * * *

UNITED STATES PATENT AND TRADEMARK OFFICE
CERTIFICATE OF CORRECTION

PATENT NO. : 5,766,944
DATED : June 16, 1998
INVENTOR(S) : Margaret E. Ruiz

It is certified that error appears in the above-indentified patent and that said Letters Patent is hereby corrected as shown below:

Title Page, [56] References Cited, PUBLICATIONS, 2nd
    Column, line 9: "thymus in SCID Mice with CD++"
    should read: -- thymus in SCID Mice with CD34+ --.
    See List of Prior Art Cited by Applicant, Item AI.

Column 12, line 34: "F(ab)" at the end of the line
    should read -- $F(ab)_2$ --.

Column 12, line 35: At the beginning of the line, delete
    -- $_2$ --.

Column 24, line 64: "more than an" should read
-- more than a --.

Signed and Sealed this

Twenty-fifth Day of August, 1998

Attest:

BRUCE LEHMAN

Attesting Officer

Commissioner of Patents and Trademarks